United States Patent [19]

van Hes et al.

[11] Patent Number: 4,572,914

[45] Date of Patent: Feb. 25, 1986

[54] INSECTICIDAL 4-SUBSTITUTED-3-CHLOROPHENYL-1-(FLUOROALKOXYPHENYLCARBAMOYL)-PYRAZOLINES

[75] Inventors: Roelof van Hes; Arnoldus C. Grosscurt, both of Weesp, Netherlands

[73] Assignee: Duphar International Research B.V., Weesp, Netherlands

[21] Appl. No.: 163,767

[22] Filed: Jun. 27, 1980

[30] Foreign Application Priority Data

Jul. 3, 1979 [NL] Netherlands .......................... 7905154

[51] Int. Cl.[4] ..................... A01N 43/56; C07D 231/06
[52] U.S. Cl. ..................................... 514/403; 548/379
[58] Field of Search ................... 548/379; 424/273 P; 514/403

[56] References Cited

U.S. PATENT DOCUMENTS 4,140,792 2/1979 Sirrenberg et al. ................. 548/379
4,174,393 11/1979 van Daalen et al. ............... 548/379

*Primary Examiner*—Richard A. Schwartz
*Assistant Examiner*—Kurt G. Briscoe
*Attorney, Agent, or Firm*—Wegner & Bretschneider

[57] ABSTRACT

The invention relates to new pyrazoline derivatives and to insecticidal compositions on the basis of the compounds.

The compositions can be used for controlling insects in a dosage from 0.01 to 1 kg of active substance per hectare.

8 Claims, No Drawings

INSECTICIDAL 4-SUBSTITUTED-3-CHLOROPHENYL-1-(FLUOROALKOXYPHENYLCARBAMOYL)-PYRAZOLINES

The invention relates to new pyrazoline derivatives and to a method of preparing the new compounds. The invention also relates to insecticidal compositions containing the new compounds and to the use of these compositions for controlling insects.

In Netherlands Patent Application No. 7800071 laid open to public inspection, substituted phenyl carbamoyl-2-pyrazolines are described having an insecticidal activity, for example, 1-(4-trifluoromethoxyphenylcarbamoyl)-3-(4-chlorophenyl)-2-pyrazoline.

It has surprisingly been found now that pyrazoline derivatives, which in particular in the 4-position deviate from the known compounds, show a significantly better insecticidal activity than the above-mentioned known compound.

The present invention is therefore characterized by new pyrazoline derivatives of the general formula:

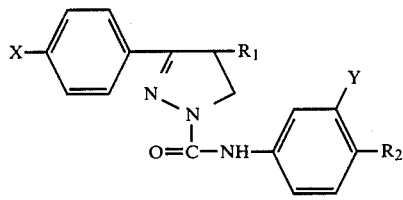

wherein $R_1$ is a substituted or non-substituted phenyl group or an alkyl group having 1 to 6 carbon atoms, which is substituted with a cyano group, an alkoxy group having 1 to 4 carbon atoms, an alkylthio group having 1 to 4 carbon atoms, an alkylsulphonyl group having 1 to 4 carbon atoms, or an alkoxycarbonyl group having 2 to 5 carbon atoms, $R_2$ is a halogenalkoxy-, halogenalkenyloxy-, halogenalkylthio-, halogenalkenylthio-, halogenalkylsulphonyl- or halogenalkenylsulphonyl group, each group having 1 to 6 carbon atoms, and X and Y are equal or different and represent hydrogen atoms or halogen atoms.

Excellently effective insecticides prove to be new compounds of the general formula

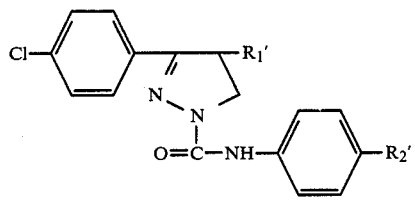

wherein $R_1'$ is a phenyl group, a halogen-substituted phenyl group or a cyanoalkyl group having 1 to 6 carbon atoms, and $R_2'$ is a halogenalkoxy- or halogenalkylthio group having 1 to 6 carbon atoms.

Examples of particularly effective insecticides are:

(1) 1-[4-(1,1,2,2-tetrafluoroethoxy)phenylcarbamoyl]-3-(4-chlorophenyl)-4-phenyl-2-pyrazoline,
(2) 1-(4-trifluoromethoxyphenylcarbamoyl)-3-(4-chlorophenyl)-4-phenyl-2-pyrazoline,
(3) 1-[4-(1,1,2,2-tetrafluoroethoxy)phenylcarbamoyl]-3-(4-chlorophenyl)-4-(2-cyanoethyl)-2-pyrazoline,
(4) 1-[4-(1,1,2,2-tetrafluoroethoxy)phenylcarbamoyl]-3-(4-chlorophenyl)-4-(3-cyanopropyl)-2-pyrazoline,
(5) 1-(4-trifluoromethoxyphenylcarbamoyl)-3-(4-chlorophenyl)-4-(3-cyanopropyl)-2-pyrazoline,
(6) 1-(4-trifluoromethylthiophenylcarbamoyl)-3-(4-chlorophenyl)-4-(3-cyanopropyl)-2-pyrazoline,
(7) 1-(4-trifluoromethylthiophenylcarbamoyl)-3-(4-chlorophenyl)-4-phenyl-2-pyrazoline,
(8) 1-[4-(1,1,2-trifluoro-2-chloroethoxy)phenylcarbamoyl]-3-(4-chlorophenyl)-4-phenyl-2-pyrazoline,
(9) 1-[4-(1,1,2-trifluoro-2-chloroethoxy)phenylcarbamoyl]-3-(4-chlorophenyl)-4-(3-cyanopropyl)-2-pyrazoline, and
(10) 1-(4-trifluoromethoxyphenylcarbamoyl)-3-(4-chlorophenyl)-4-(4-chlorophenyl)-2-pyrazoline.

Other new pyrazoline derivatives according to the invention which have a strong insecticidal activity are:

(11) 1-[3-chloro-4-(1,1,2-trifluoro-2-chloroethoxy)phenylcarbamoyl]-3-(4-chlorophenyl)-4-phenyl-2-pyrazoline,
(12) 1-[3-chloro-4-(1,1,2-trifluoro-2-chloroethoxy)phenylcarbamoyl]-3-(4-chlorophenyl)-4-(3-cyanopropyl)-2-pyrazoline,
(13) 1-(4-trifluoromethylsulphonylphenylcarbamoyl)-3-(4-chlorophenyl)-4-(3-cyanopropyl)-2-pyrazoline,
(14) 1-(4-trifluoromethylsulphonylphenylcarbamoyl)-3-(4-chlorophenyl)-4-phenyl-2-pyrazoline,
(15) 1-[4-(1,1,2,2-tetrafluoroethoxy)phenylcarbamoyl]-3-(4-chlorophenyl)-4-(2-ethylthioethyl)-2-pyrazoline,
(16) 1-(4-trifluoromethoxyphenylcarbamoyl)-3-(4-chlorophenyl)-4-(2-ethylthioethyl)-2-pyrazoline,
(17) 1-(4-trifluoromethoxyphenylcarbamoyl)-3-(4-chlorophenyl)-4-(2-methoxyethyl)-2-pyrazoline,
(18) 1-(4-trifluoromethylthiophenylcarbamoyl)-3-(4-chlorophenyl)-4-(2-methoxyethyl)-2-pyrazoline, and
(19) 1-(4-trifluoromethylsulphonylphenylcarbamoyl)-3-(4-chlorophenyl)-4-(2-methoxyethyl)-2-pyrazoline.

The substances according to the invention may be used for the control of mites and insects in agriculture and horticulture, in woods and in surface waters, as well as for the protection of textiles against attack by, for example, moths and carpet beetles, and against insects in stores, for example, in stored cereals. The substances according to the invention may also be used for controlling insects living in the manure of hot-blooded animals, for example, cows, pigs and hens. For this application the active compounds—for example, mixed through the food—can be administered orally to the animals, so that in the course of time the substances land in the manure ("through-feeding").

Due to their high insecticidal activity the compounds according to the invention in small dosages already are capable of effectively controlling noxious insects, for example, beetles, flies, mosquitos; it has been found that the compounds in accordance with the invention are particularly active against the larvae of these insects.

For practical applications the substances in accordance with the invention are usually processes to compositions. In such compositions the active substance is mixed with solid carrier material or dissolved or dispersed in liquid carrier material, if desired in combination with auxiliary substances, for example, emulsifiers, wetting agents, dispersion agents and stabilizers.

Examples of compositions according to the invention are aqueous solutions and dispersions, oily solutions and oily dispersions, solutions in organic solvents, pastes, dusting powders, dispersing powders, miscible oils, granules, pellets, invert emulsions, aerosol compositions, fumigating candles.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus by smulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/-separation if desired in the presence of a binder, on granular carrier material, for example porous granules (for example pumice and attaclay), mineral non-porous granules (sand or ground marlow), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, or glycol ether, to which solution a dispersion agent and, if desired, a surface-active substance has been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

Insecticides, for example 1. organic chlorine compounds, for example 6,7,8,9,10,10-hexachloro-1,5,5a,6,9,9a-hexahydro-6,9-methano-2,4,3-benzo[e]dioxathiepine-3-oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethyl phosphate;
4. O,O-di(m)ethyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-6-methylpyrimidin-4-yl-, and O-4-nitrophenyl O,O-di(m)ethyl phosphorothioate;
5. O,O-di(m)ethyl phosphorodithioates, for example, S-methylcarbamoylmethyl-, S-2-etylthioethyl-, S-(3,4-dihydro-4-oxobenzo[d]-1,2,3-triazin-3-ylmethyl)-, S-1,2-di(ethoxycarbonyl)ethyl-, S-6-chloro-2- oxobenzoxazolin-3-ylmethyl-, and S-2,3-dihydro-5-methoxy-2-oxo-1,3,4-thiadiazol-3-ylmethyl O,O-di(m)ethyl phosphorodithioate;
6. phosphonates, for example, dimethyl 2,2,2-trichloro-1-hydroxyethylphosphonate;
7. benzoylurea, for example, N-(2,6-difluorobenzoyl)-N'-(4-chlorophenyl)urea;
8. natural and synthetic pyrethroids;
9. amidines, for example, N'-(2-methyl-4-chlorophenyl)-N,N-dimethylformamidine; and
10. microbial insecticides, such as Bacillus thuringiensis.

Acaricides, for example 1. organic tin compounds, for example, tricyclohexyl tin hydroxide and di[tri-(2-methyl-2-phenylpropyl)tin-]oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;

and furthermore: 3-chloro-α-ethoxyimino-2,6-dimethoxybenzyl benzoate and O,O-dimethyl S-methylcarbamoyl methyl phosphorothioate.

Fungicides, for example 1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole(-2)carbamates and 1,2-bis(3-alkoxycarbonyl-2-thiureido)benzene, and furthermore 2,4-dinitro-6-(2-acetylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropylcarbamoyl)-3-(3,5-dichlorophenyl)hydantoin, N-(1,1,2,2-tetrachloroethylthio)-4-cyclohexene-1,2-carboximide, N-trichloromethylmercapto-4-cyclohexene-1,2-dicarboximide, and N-tridecyl-2,6-dimethylmorpholine.

The dosages of the composition according to the invention desired for practical application will, of course, depend on various factors, for example, field of application, selected active substance, form of composition, nature and extent of the infestation and the weather conditions.

In general it holds that favourable results are achieved with a dosage which corresponds to 0.01 to 1 kg of the active substance per hectare.

For the above-described "through-feeding" the active substance is mixed through the fodders in a quantity effective for insecticidal application.

The compounds according to the invention are new substances which can be prepared in a manner known per se for related compounds.

For example, the new compounds can be prepared by reacting a pyrazoline of the general formula

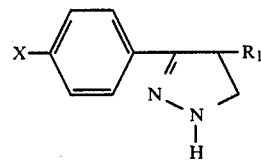

wherein $R_1$ and X have the above meanings, with an isocyanate of the general formula

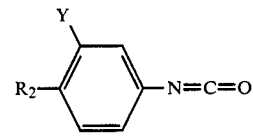

wherein $R_2$ and Y have the meanings also given above. This reaction is carried out in a suitable solvent, for example, an ether, for example, diethyl ether, an aliphatic nitrile, for example, acetonitrile, a chlorinated aliphatic hydrocarbon, or an aromatic hydrocarbon, at a temperature between 0° C. and the boiling-point of the solvent used, preferably at room temperature.

The invention will now be described in greater detail with reference to the following specific examples.

EXAMPLE I

Preparation of 1-[4-(1,1,2,2-tetrafluoroethoxy)phenylcarbamoyl]-3-(4-chlorophenyl)-4-phenyl-2-pyrazoline 1.7 g of 4-(1,1,2,2-tetrafluoroethoxy)phenylisocyanate were added, while stirring, to a suspension of 1.8 g of 3-(4-chlorophenyl)-4-phenyl-2-pyrazoline in 40 ml of dry diethyl ether. After stirring at room temperature for approximately 1 hour 40 ml of petroleum ether (40–60) were added to the reaction mixture, after which stirring at room temperature was continued for another 3 hours. The precipitate formed was sucked off and washed with petroleum ether (40–60). The desired product was obtained in a yield of 3.1 g; melting-point 178°–180° C.

In a corresponding manner in which, however, the addition of petroleum ether was omitted in some cases, the following compounds were prepared:

1-(4-trifluoromethoxyphenylcarbamoyl)-3-(4-chlorophenyl)-4-phenyl-2-pyrazoline; melting-point 175°–176° C.;

1-[4-(1,1,2,2-tetrafluoroethoxy)phenylcarbamoyl]-3-(4-chlorophenyl)-4-(2-cyanoethyl)-2-pyrazoline; melting-point 183°–186° C.;

1-[4-(1,1,2,2-tetrafluoroethoxy)phenylcarbamoyl]-3-(4-chlorophenyl)-4-(3-cyanopropyl)-2-pyrazoline; melting-point 175°–177° C.;

1-(4-trifluoromethoxyphenylcarbamoyl)-3-(4-chlorophenyl)-4-(3-cyanopropyl)-2-pyrazoline; melting-point 155°–160° C.;

1-[4-(1,1,2,2-tetrafluoroethoxy)phenylcarbamoyl]-3-(4-chlorophenyl)-4-(2-ethylthioethyl)-2-pyrazoline; melting-point 108°–114° C.;

1-(4-trifluoromethoxyphenylcarbamoyl)-3-(4-chlorophenyl)-4-(2-ethylthioethyl)-2-pyrazoline; melting-point 103°–108° C.;

1-(4-trifluoromethoxyphenylcarbamoyl)-3-(4-chlorophenyl)-4-(2-methoxyethyl)-2-pyrazoline; melting-point 119°–121° C.;

1-(4-trifluoromethylthiophenylcarbamoyl)-3-(4-chlorophenyl)-4-(3-cyanopropyl)-2-pyrazoline; melting-point 183°-185° C.;

1-(4-trifluoromethylthiophenylcarbamoyl)-3-(4-chlorophenyl)-4-phenyl-2-pyrazoline; melting-point 212°-213° C.;

1-(4-trifluoromethylsulphonylphenylcarbamoyl)-3-(4-chlorophenyl)-4-(3-cyanopropyl)-2-pyrazoline; melting-point 178°-181° C.;

1-(4-trifluoromethylsulphonylphenylcarbamoyl)-3-(4-chlorophenyl)-4-phenyl-2-pyrazoline; melting-point 183°-185° C.;

1-(4-trifluoromethylthiophenylcarbamoyl)-3-(4-chlorophenyl)-4-(2-methoxyethyl)-2-pyrazoline; melting-point 154°-156° C.;

1-(4-trifluoromethylsulphonylphenylcarbamoyl)-3-(4-chlorophenyl)-4-(2-methoxyethyl)-2-pyrazoline; melting-point 149°-152° C.;

1-[4-(1,1,2-trifluoro-2-chloroethoxy)phenylcarbamoyl]-3-(4-chlorophenyl)-4-phenyl-2-pyrazoline; melting-point 162° C.;

1-[3-chloro-4-(1,1,2-trifluoro-2-chloroethoxy)phenylcarbamoyl]-3-(4-chlorophenyl)-4-phenyl-2-pyrazoline; melting-point 170° C.;

1-[4-(1,1,2-trifluoro-2-chloroethoxy)phenylcarbamoyl]-3-(4-chlorophenyl)-4-(3-cyanopropyl)-2-pyrazoline; melting-point 171° C.;

1-[3-chloro-4-(1,1,2-trifluoro-2-chloroethoxy)phenylcarbamoyl]-3-(4-chlorophenyl)-4-(3-cyanopropyl)-2-pyrazoline; melting-point 77° C.; and 1-(4-trifluoromethoxyphenylcarbamoyl)-3-(4-chlorophenyl)-4-(4-chlorophenyl)-2-pyrazoline; melting-point 159° C.

EXAMPLE II

The compounds according to the invention were processed to compositions by suspending the compounds in water in the presence of a dispersion agent, for example, lignine sulphonate, and/or a wetting agent, for example naphthalene sulphonate, an alkyl sulphate, an alkyl benzene sulphonate, an alkylpolyoxyethylene or an alkylarylpolyoxyethylene.

Young plants of Brussels sprouts of approximately 15 cm high were sprayed with the compositions thus obtained in various concentrations. After the plants had dried, they were placed in cylinders of plexiglass and then infected with 5 larvae of *Pieris brassicae* (caterpillars of the cabbage white butterfly). The cylinders were then covered with a gauze and shelved in which a light-dark cycle of 18 hours light and 6 hours dark was used; temperature in the light 24° C., relative humidity 70%; temperature in the dark 19° C., relative humidity 80-90%.

After 5 days the mortality percentage of the larvae was established. Each experiments was carried out in triplicate. The results of the experiments are recorded in Table A below. The numbers of the compounds correspond to the numbers used before in this specification.

TABLE A

Insecticidal activity against larvae of Pieris brassicae

| active compound | Concentration in mg of act. subst. p. 1. | Mortality percentage |
| --- | --- | --- |
| 1-(4-trifluoromethoxyphenylcarbamoyl)-3-(4-chlorophenyl)-2-pyraxoline (known) | 30 | 90-100 |
|  | 3 | 0-50 |
| (1) | 30 | 90-100 |
|  | 3 | 90-100 |

TABLE A-continued

Insecticidal activity against larvae of Pieris brassicae

| active compound | Concentration in mg of act. subst. p. 1. | Mortality percentage |
| --- | --- | --- |
|  | 0.3 | 90-100 |
| (2) | 30 | 90-100 |
|  | 3 | 90-100 |
|  | 0.3 | 90-100 |
| (3) | 30 | 90-100 |
|  | 3 | 90-100 |
|  | 0.3 | 90-100 |
| (4) | 30 | 90-100 |
|  | 3 | 90-100 |
|  | 0.3 | 90-100 |
| (5) | 30 | 90-100 |
|  | 3 | 90-100 |
|  | 0.3 | 90-100 |
| (6) | 30 | 90-100 |
|  | 3 | 90-100 |
|  | 0.3 | 50-90 |
| (7) | 30 | 90-100 |
|  | 3 | 90-100 |
|  | 0.3 | 90-100 |
| (8) | 30 | 90-100 |
|  | 3 | 90-100 |
|  | 0.3 | 90-100 |
| (9) | 30 | 90-100 |
|  | 3 | 90-100 |
|  | 0.3 | 50-90 |
| (10) | 30 | 90-100 |
|  | 3 | 90-100 |
|  | 0.3 | 90-100 |
| (11) | 30 | 90-100 |
|  | 3 | 90-100 |
|  | 0.3 | 0-50 |
| (12) | 30 | 90-100 |
|  | 3 | 90-100 |
|  | 0.3 | 0-50 |
| (13) | 30 | 90-100 |
|  | 3 | 90-100 |
|  | 0.3 | 50-90 |
| (14) | 30 | 90-100 |
|  | 3 | 90-100 |
|  | 0.3 | 0-50 |
| (15) | 30 | 90-100 |
|  | 3 | 90-100 |
|  | 0.3 | 0-50 |
| (16) | 30 | 90-100 |
|  | 3 | 90-100 |
|  | 0.3 | 0-50 |
| (17) | 30 | 90-100 |
|  | 3 | 90-100 |
|  | 0.3 | 0-50 |
| (18) | 30 | 90-100 |
|  | 3 | 90-100 |
|  | 0.3 | 0-50 |
| (19) | 30 | 90-100 |
|  | 3 | 90-100 |
|  | 0.3 | 0-50 |

EXAMPLE III

Young potato plants, approximately 15 cm high, were sprayed with the compositions obtained according to Example II in various concentrations. After the plants had dried, cylinders of Plexiglass were placed over the plants. The plants were then infected with 10 larvae of *Leptinotarsa decemlineata* (larvae of the Colorado beetle) and shelved as indicated in Example III. After 5 days the mortality percentage of the larvae was established. The results of the experiments are recorded in Table B below.

The numbers of the compounds correspond to the numbers used before in this specification.

TABLE B

Insecticidal activity against larvae of Leptinotarsa decemlineata

| active compound | Concentration in mg of act. subst. p.l. | Mortality percentage |
|---|---|---|
| (1) | 3 | 90–100 |
| | 1 | 90–100 |
| | 0.3 | 90–100 |
| | 0.1 | 90–100 |
| (2) | 3 | 90–100 |
| | 1 | 90–100 |
| | 0.3 | 90–100 |
| | 0.1 | 90–100 |
| (3) | 3 | 90–100 |
| | 1 | 90–100 |
| | 0.3 | 90–100 |
| (4) | 3 | 90–100 |
| | 1 | 90–100 |
| | 0.3 | 90–100 |
| | 0.1 | 90–100 |
| (5) | 3 | 90–100 |
| | 1 | 90–100 |
| | 0.3 | 90–100 |
| | 0.1 | 50–90 |
| (6) | 3 | 90–100 |
| | 1 | 90–100 |
| | 0.3 | 90–100 |
| (7) | 3 | 90–100 |
| | 1 | 90–100 |
| | 0.3 | 90–100 |
| (8) | 3 | 90–100 |
| | 1 | 90–100 |
| | 0.3 | 50–90 |
| (9) | 3 | 90–100 |
| | 1 | 90–100 |
| | 0.3 | 50–90 |
| (10) | 3 | 90–100 |
| | 1 | 90–100 |
| | 0.3 | 50–90 |
| (11) | 3 | 90–100 |
| | 1 | 90–100 |
| | 0.3 | 50–90 |
| (12) | 3 | 50–90 |
| | 1 | 50–90 |
| | 0.3 | 50–90 |
| (13) | 3 | 90–100 |
| | 1 | 90–100 |
| (14) | 3 | 90–100 |
| | 1 | 90–100 |
| | 0.3 | 90–100 |
| (15) | 3 | 90–100 |
| | 1 | 90–100 |
| | 0.3 | 90–100 |
| (16) | 3 | 90–100 |
| | 1 | 90–100 |
| | 0.3 | 50–90 |
| | 0.1 | 0–50 |
| (17) | 3 | 90–100 |
| | 1 | 90–100 |
| | 0.3 | 50–90 |
| | 0.1 | 0–50 |
| (18) | 3 | 90–100 |
| | 1 | 90–100 |
| | 0.3 | 90–100 |
| (19) | 3 | 90–100 |
| | 1 | 0–50 |

We claim:
1. 1-(4-trifluoromethoxyphenylcarbamoyl)-3-(4-chlorophenyl)-4-phenyl-2-pyrazoline.
2. 1-[4-(1,1,2,2-tetrafluoroethoxy)phenylcarbamoyl]-3-(4-chlorophenyl)-4-(3-cyanopropyl)-2-pyrazoline.
3. 1-(4-trifluoromethoxyphenylcarbamoyl)-3-(4-chlorophenyl)-4-(3-cyanopropyl)-2-pyrazoline.
4. An insecticidal composition comprising an insecticidally effective amount of a pyrazoline compound selected from the group consisting of 1-(4-trifluoro-methoxyphenylcarbamoyl)-3-(4-chlorophenyl)-4-phenyl-2-pyrazoline, 1-[4-(1,1,2,2-tetrafluoroethoxy)phenylcarbamoyl]-3-(4-chlorophenyl)-4-(3-cyanopropyl)-2-pyrazoline, and 1-(4-trifluoromethoxyphenylcarbamoyl)-3-(4-chlorophenyl)-4-(3-cyanopropyl)-2-pyrazoline and a solid or liquid inert carrier.
5. A composition as claimed in claim 4, characterized in that the active constituent is 1-(4-trifluoromethoxyphenylcarbamoyl)-3-(4-chlorophenyl)-4-phenyl-2-pyrazoline.
6. A composition as claimed in claim 4, characterized in that the active onstituent is 1-[4-(1,1,2,2-tetrafluoroethoxy)phenylcarbamoyl]-3-(4-chlorophenyl)-4-(3-cyanopropyl)-2-pyrazoline.
7. A composition as claimed in claim 4, characterized in that the active constituent is 1-(4-trifluoromethoxyphenylcarbamoyl)-3-(4-chlorophenyl)-4-(3-cyanopropyl)-2-pyrazoline.
8. A method of controlling insects, characterized in that the infested area is treated with a composition of claim 4, 5, 6, or 7 in a dosage from 0.01 to 1 kg of active substance per hectare.

* * * * *